United States Patent [19]

Nelson et al.

[11] Patent Number: 4,628,096

[45] Date of Patent: Dec. 9, 1986

[54] PREPARATION OF 2-HALO-5-METHYLPYRIDINES FROM 4-METHYL-4-PENTENE DERIVATIVES

[75] Inventors: Richard V. Nelson, Wilmington, Del.; John F. Stephen, West Chester, Pa.

[73] Assignee: ICI Americas Inc., Wilmington, Del.

[21] Appl. No.: 684,149

[22] Filed: Dec. 20, 1984

Related U.S. Application Data

[62] Division of Ser. No. 496,680, May 20, 1983, Pat. No. 4,504,664.

[51] Int. Cl.[4] ............................................. C07D 213/61
[52] U.S. Cl. ................................ 546/250; 546/345; 546/219; 549/561
[58] Field of Search ............................... 546/250, 345

[56] References Cited

U.S. PATENT DOCUMENTS 4,584,380 4/1986 Hartmann et al. .................. 546/250

*Primary Examiner*—Robert T. Bond
*Attorney, Agent, or Firm*—John Wilson Jones

[57] ABSTRACT

A method of preparing certain 2-halo-5-methylpyridines, useful as herbicide intermediates, is presented starting from acyclic pentenes. The pentene is difunctionalized, e.g., by making the epoxide, and is then reacted with a nitrogen source to close the ring. The nitrogen-containing 6-membered heterocycle may then be aromatized readily to produce the 2-halo-5-methylpyridine desired. Also part of the invention are novel acyclic and cyclic intermediates used in the process.

19 Claims, No Drawings

PREPARATION OF 2-HALO-5-METHYLPYRIDINES FROM 4-METHYL-4-PENTENE DERIVATIVES

This is a divisional of co-pending application Ser. No. 06/496,680 filed on May 20, 1983, now U.S. Pat. No. 4,504,664.

BACKGROUND OF THE INVENTION

It is known that 2-halogen-5-methylpyridines are useful as starting materials or intermediates in the synthesis of herbicides of the pyridyloxyphenoxy type. Examples of 4-(5-halomethyl-2-pyridyloxy)phenoxy compounds useful as herbicides are disclosed in European Published Patent Application No. 483, United Kingdom Patent Specification Nos. 1,599,121 and 1,599,126 and U.S. Pat. Nos. 4,184,041 and 4,317,913. For example, butyl 2-[4-(5-trifluoromethyl-2-pyridyloxy)phenoxy]propionate which is also known as fluazifop-butyl is an effective grass herbicide which can be used in fields where broad-leaved crops such as cotton and soybeans are cultivated. Important starting materials for such pyridyloxyphenoxy compounds are the 2-halo-5-trichloromethylpyridines such as 2-chloro-5-trichloromethylpyridine described in U.S. Pat. No. 4,317,913. Such 2-halo-5-trichloromethylpyridines, in turn, may be prepared by chlorinating, under ultraviolet light irradiation, a 2-halo-5-methylpyridine as described in U.S. Pat. No. 4,152,328.

One object of the present invention is a new process for the synthesis of 2-halo-5-methylpyridines which are known to be useful in the synthesis of herbicides. Such a novel process would be efficient in that a single starting material (II) may be reacted via at least two alternative steps to produce at least two different intermediates which all may be taken on to produce a single compound. With such a process, one can plan on using a single starting material and producing a single final product while retaining processing flexibility by the ability to alter reagents and reaction conditions since one can carry the process through different intermediates of the formula (III) during the process of the invention.

A further object of the present invention is a process for preparing 2-halo-5-methylpyridines which includes cyclization of a 4-methylpentane derivative with an amine whereby the direct product of the cyclization has the correct oxidation state for the desired aromatic pyridine.

SUMMARY OF THE INVENTION

According to the present invention, a 2-halo-5-methylpyridine of the following formula (I):

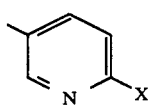
(I)

X being a halogen such as a chlorine, bromine or fluorine atom, is prepared by (a) functionalizing the two alkene carbons of the pentene derivative of the following formula (II):

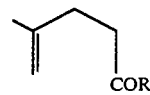
(II)

R being a leaving group to be displaced in the following step, (b) reacting the product of (a) with an amine to produce is a 5-methyl-2-pyridone with functionality at the 1- and 5-positions and, therefore, the same oxidation state as the desired product 2-halo-5-methylpyridine, and (c) reacting the product of step (b) with a halogenation agent to convert the pyridone oxo to a vinyl halide and aromatization of the ring to produce the desired 2-halo-5-methylpyridine of the formula (I). Also part of the present invention are novel intermediates.

DETAILED DESCRIPTION OF THE INVENTION

The starting material utilized in the process of the present invention is a 4-methyl-4-pentene of the following formula (II):

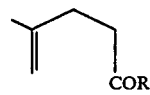
(II)

wherein R is a leaving group displaceable by an amine. Representative leaving groups include halo, aryloxy or alkoxy groups, the aryloxy and alkoxy groups being substituted or unsubstituted. Specific examples include, chloro, bromo, phenoxy, benzyloxy or alkoxy groups of about 1 to 6 carbons. The synthesis of starting materials of the formula (II) is described by J. J. Ritter et al. in the Journal of Organic Chemistry, Vol. 27, pages 622–623 (1962); M. Julia et al. Bull. Soc. France, pages 2415–2427 (1969); W. S. Johnson et al. in the Journal of the American Chemical Society, Vol. 92, pages 741–743 (1970); J. E. McMurray et al. in the Journal of Organic Chemistry, Vol. 40, pages 2556–2557 (1975); and in U.S. Pat. Nos. 3,642,834 issued Feb. 15, 1972 and 4,234,741 issued Nov. 18, 1980.

In the first step (a) of the process of the present invention, a compound of formula (II) is reacted with an agent which reacts, across the double bond of (II), to produce the pentane derivative of the following formula (III):

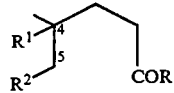
(III)

wherein $R^1$ and $R^2$ are independently chosen and are heteroatomic moieties or are joined together to form a heterocyclic ring wherein the atom or atoms of $R^1$ and $R^2$ which are directly attached to carbons 4 and 5 are heteroatoms. Examples of $R^1$ and $R_2$, which may be the same or different, are alkanoyloxy of about 1 to 4 carbons, hydroxy or halogen groups, e.g., chlorine or bromine atoms. Alternatively, $R^1$ and $R^2$ are joined to form a 3-membered heterocyclic ring, e.g., an oxirane (epoxide) ring. Preferably, $R^1$ is hydroxy and $R^2$ is bromine or chlorine; $R^1$ and $R^2$ are both bromine or chlorine; or $R^1$ and $R^2$ are joined to form an oxirane ring.

Various agents such as halohydrination, haloalkanoyloxylation, halogenation and oxidation agents may be used in the first step (a) of the invention.

In a first embodiment of the first step (a) of the process, the pentene of formula (II) is reacted with a halohydrination or haloalkanoyloxylation agent, i.e., an agent which produces a compound of formula (III) wherein one of $R^1$ and $R^2$ is hydroxy and the other is halogen or an agent which provides (III) wherein one of $R^1$ and $R^2$ is alkanoyloxy and the other is halogen. The halohydrination agent may be a bromohydrination or chlorohydrination agent to result in one of $R^1$ and $R^2$ being hydroxy and the other being a halogen such as bromine or chlorine in formula (III). Examples of such agents include alkali metal hypohalites, such as sodium hypohalite and sodium hypobromite, N-bromosuccinimide, N-chlorosuccinimide, bromine, 1,3-dibromo or 1,3-dichloro-5,5-dimethylhydantoin, chloramine-T hydrate, N-bromoacetamide and N-chloroacetamide. Reaction conditions for the halohydrination will vary according to the particular agent used but in general, the reaction is conducted in the presence of water and, optionally, a cosolvent such as a halogenated aliphatic, e.g., chloroform, an ether, e.g., diethyl ether, a formamide, e.g., dimethylformamide, dimethylsulfoxide or a ketone, e.g., acetone. The temperature of the reaction can be from about 0° to 70° C. with a molar ratio of about 1:1 to 2:1, agent:compound of formula (II). For N-bromosuccinimide, the temperature will be about 0° to 25° C. with the use of an ether or halogenated aliphatic solvent. The haloalkanoyloxylation agent may be a hypohalite of an aliphatic carboxylic acid of about 2–4 carbons or two or more compounds which generate such a hypohalite, examples being any of the halohydination agents described above together with an aliphatic carboxylic acid of about 2 to 4 carbons, or a salt thereof. Examples of such agents include acetyl hypobromite, propanoyl hypochlorite, chloramine-T hydrate with acetic acid and N-bromoacetamide with lithium acetate. The haloalkanoyloxylation is carried out in an organic solvent, preferably in the parent aliphatic carboxylic acid of the hypohalite e.g., acetic, propanoic or butyric acid, most preferably in acetic acid. The haloalkanoyloxylation may be carried out from about 0° to 40° C. using an equimolar or, preferably, a molar excess of the agent. Usually, the hydroxy or alkanoyloxy moieties will be the $R^1$ group, in view of the greater stability of the 4-position carbonium ion compared to the 5-position ion.

In a second embodiment of the first step (a) of the process, the pentene of formula (II) is reacted in the absence of water with a halogenation agent such as a bromination or a chlorination agent, e.g. bromine or chlorine. The reaction may be conducted at a temperature of about −10° to 30° C., in a solvent such as a halogenated aliphatic or halogenated aromatic solvent, e.g. methylene chloride. The product of the second embodiment is the pentane of formula (III) wherein $R^1$ and $R^2$ are each the same halogen, e.g., $R^1$ and $R^2$ are both bromine or both chlorine.

In a third embodiment of the first step (a) of the process, the pentene of formula (II) is reacted with an oxidation agent such as a peracid of the formula $R^4$—COOOH wherein $R^4$ is an organic moiety such as alkyl, with examples of the peracid being peracetic, peroxytrifluoroacetic, perbenzoic, monoperphthalic and metachloroperbenzoic acids. Other oxidation agents include alkylhydroperoxides, e.g. tert-butylhydroperoxide, used with a transition metal catalyst such as vanadium and hydrogen peroxide used with a catalyst such as tungsten. The product of the oxidation is an epoxide of the formula (III) wherein $R^1$ and $R^2$ are joined to form a 3-membered oxygen-containing ring, i.e., of the formula $CH_3—C(OCH_2)—CH_2—CH_2—COR$. The oxidation reaction may be conducted at a temperature of about 0° to 120° C., e.g., about 20° to 50° C. in a solvent such as an ester, e.g. ethyl acetate or a halogenated aliphatic such as methylene chloride. When using a peracid for the oxidation, the reaction may be conducted in the presence of an aqueous buffer solution, e.g., of sodium bicarbonate, in order to reduce the possibility of opening the epoxide ring.

In the second step (b) of the process of the present invention, the pentane derivative of formula (III) is reacted with an amine of the formula $H_2NR^3$ to produce a pyridone of the following formula (IV):

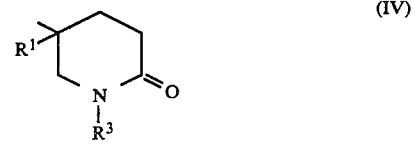

wherein $R^3$ is a heteroatomic moiety and wherein the atom of $R^3$ which is directly attached to the nitrogen atom is a heteroatom. Examples of $R^3$ groups are alkoxy of about 1 to 6 carbons, alkanoyloxy of about 1 to 6 carbons or hydroxy, preferably hydroxy. Amines which can be reacted with a formula (III) compound include methoxyamine, hydroxylamine and salts thereof, e.g., methoxyamine hydrochloride and hydroxylamine sulfate or hydrochloride. The cyclization reaction may be carried out at about room temperature to about 100° C. in an aqueous medium such as water or a water-ethanol, water-dioxane or water-tetrahydrofuran solvent system in at least an equimolar ratio of reagent:starting material of formula (III).

In the third step (c) of the process of the present invention, the pyridone of formula (IV) is reacted with a halogenation agent to produce the 2-halo-5-methylpyridine of formula (I) with a net loss of $HR^1$ and $HR^3$. Such reagents include oxalyl chloride, thionyl bromide, thionyl chloride, phosgene and phosphorus oxychloride. Step (c) of the invention may be conducted at a temperature of about room temperature to 80° C., e.g., about 25° to 40° C., in a solvent such as an aromatic or chlorinated aliphatic hydrocarbon, e.g., methylene chloride.

The process described above may be modified to produce a compound of the following formula (V)

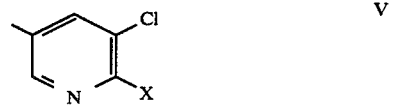

wherein X is a halogen. The 3-chloro-2-halo-5-methylpyridine of formula (V) is known as an intermediate in the synthesis of herbicides as disclosed in U.S. Pat. Nos. 4,184,041 and 4,324,627. If the pentene of formula (II) is chlorinated with chlorine in the first step (a) of the invention, it is possible to overchlorinate the starting material and obtain the pentane of the following formula (VI) which may be then reacted as described above in step (b) to produce a pyridone of the formula (VII):

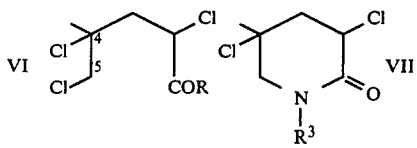

wherein $R^3$ is as described above. In the final step (c), the pyridone (VII) is reacted with a halogenation agent as described above to produce the pyridine of formula (V). In this overchlorination step (a) the reaction is conducted at about 30° to 80° C. in a solvent such as a halogenated aliphatic or halogenated aromatic solvent, e.g., carbon tetrachloride. Preferably, the progress of the chlorination is monitored by a technique such as gas chromatography to ensure the correct amount of chlorine reaction with the compound of formula (II).

Also part of the present invention are intermediates of the formula (III) as defined above with the proviso that $R^1$ and $R^2$ are not both chlorine atoms and compounds of formula (IV).

In the following Examples and throughout the specification, the following abbreviations are used: °C. (degrees Centigrade); ml (milliliters); g (grams); m (moles); cm (centimeters); mmoles (millimoles); bp (boiling point); mm (millimeters); mp (melting point); GC (gas chromatography); NMR (nuclear magnetic resonance spectrum); MS (mass spectrum); m/e (mass to charge ratio); M+ (molecular ion); IR (infrared spectrum); and C,H,N, etc. (the conventional symbols for the elements). In addition, the following abbreviations are used for NMR: s (singlet); t (triplet); st (split triplet); q (quintuplet); dd (double doublet); bs (broad singlet); m (multiplet); b (broad); J (coupling constant); Hz (Hertz); and $d_6$-DMSO (deuterated dimethyl sulfoxide).

EXAMPLE 1 a. Ethyl 4-methyl-4-pentenoate

A solution of 12.7 g of methallyl alcohol (0.176 mol), 225 ml of triethyl orthoacetate (1.23 m) and 0.78 g of propionic acid (0.011 m) was heated to a temperature of 130°–145° C. (external). The reaction flask was equipped with an apparatus suitable for the continuous removal of the produced ethanol. When the distillation of the ethanol ceased after about 3 hours the apparatus was removed and a normal Vigreaux head was attached. The pressure was reduced to 100 mm of Hg and the excess triethyl orthoacetate was distilled off until the temperature began to move higher. After cooling the remaining liquid was treated with 300 ml of 10% $KH_2PO_4$ and permitted to stir at room temperature for 90 minutes. The product was subsequently isolated by separating the olefinic ester from the aqueous layer and extracting the aqueous layer with ether 3 times, 100 ml each. The organic portions were combined, dried with $MgSO_4$, and concentrated. The crude weight of the colorless liquid was 27.5 g. GC showed only product contaminated with volatiles such as solvent. Distillation yielded 21.3 g (85.2% yield) of pure ester: bp 158°–163° C.

b. Ethyl 5-bromo-4-hydroxy-4-methyl pentanoate

To a solution of 2.97 g (0.021 m) of ethyl 4-methyl-4-pentenoate in 20 ml of ether was added 20 ml of water. The reaction mixture was cooled in an ice-water bath and 3.72 g (0.021 m) of N-bromosuccinimide was added portionwise over about 5 minutes. The biphasic mixture was allowed to stir with gradual warming to room temperature. Inspection of the reaction mixture by GC after 3 hours indicated that no starting olefin remained. The reaction was worked up by separating the two layers and extracting the aqueous layer with ether. The combined organic layers was dried with $MgSO_4$ and subsequently concentrated to yield a colorless liquid. The crude weight was 4.97 g (>99% of theoretical recovery: >85% purity)

NMR($CDCl_3$,$\delta$): 4.13 (q, 2H), 3.40 (s, 2H), 2.63–2.33 (m, 3H), 1.95 (st, 2H), 1.30 (s, 3H), 1.25 (t, 3H).

MS: m/e (M+-15) 223, 225; (M+-$C_2H_5OH$) 193, 195; 177 and 179 (7%); 99 (100%).

EXAMPLE 2

1,5-Dihydroxy-5-methyl-2-piperidinone (via bromohydrin)

To a mixture of 4.12 g (25.1 mmoles) of hydroxylamine sulfate in 10 ml of water was added slowly a 5 ml aqueous solution of 2.00 g (50.2 mmoles) of sodium hydroxide. To this was then added 1.15 g (4.8 mmoles) of the bromohydrin produced in Example 1b. in the reaction flask with the aid of a small amount of ethanol (<1 ml). The mixture was heated to reflux and stirred for 5½ hours before being cooled to room temperature. The reaction mixture was concentrated to yield a yellow moist solid which was dissolved in acetone and concentrated. Methanol was then added, the insoluble sodium sulfate removed by filtration and the solvent was evaporated. Trituration with acetone yielded 170 mg of a white solid. Further manipulation yielded another 134 mg of material. The total weight obtained was 304 mg (44% yield). This material had a proton NMR spectrum identical to the piperidinone obtained from Example 4.

EXAMPLE 3

Ethyl 4,5-expoxy-4-methyl pentanoate

To a solution of 14.22 g (0.10 m) of ethyl 4-methyl-4-pentenoate in 300 ml of methylene chloride was added a solution of 250 ml of 0.5 Normal aqueous sodium bicarbonate. This biphasic solution was cooled in an ice-water bath and 22.33 g (0.11 m, 85–90% purity) of metachloroperbenzoic acid was added portionwise over a period of 15 minutes. Upon completion of the addition the mixture was allowed to stir with cooling for another 90 minutes and was then allowed to warm to room temperature and stir for an additional 2 hours. Inspection of the reaction mixture by GC after 3½ hours indicated it to be 95% complete. Workup was effected by separating the two layers, washing the organic layer with 10% aqueous $Na_2SO_3$ 2 times, 100 ml each, and finally with water. The solution was dried with $Na_2SO_4$ and concentrated to yield a pale yellow liquid. The crude weight was 15.5 g (98% of the theoretical, >90% purity); bp 88°–90° C. at 2.2 mm of $H_g$.

NMR($CDCl_3$ in $\delta$): 4.05 (q, 2H), 2.52 (s, 2H), 2.31 (split t, 2H), 1.80 (split t, 2H), 1.26 (s, 3H), and 1.20 (t, 3H)

MS: m/e(M+-$C_2H_5OH$) 112 (65%); 88 (92%); 84 (56%); 69 (35%); 55 (100%); 41 (81%)

IR: 1738 $cm^{-1}$ (C=O)

EXAMPLE 4

1,5-Dihydroxy-5-methyl-2-piperidinone (via epoxide)

To a mixture of 28.27 g (0.172 m) of hydroxylamine sulfate in 25 ml of water was added slowly a 25 ml aqueous solution of 13.80 g (0.344 m) of sodium hydroxide. To the resulting solution was added 5.45 g (0.034 m) of ethyl 4,5-epoxy-4-methylpentanoate with the aid of 2 ml of ethanol. The mixture was heated to reflux and stirred for 17 hours. The reaction mixture was cooled and concentrated under reduced pressure to yield a yellow moist solid. The solid was washed with methanol several times and the methanol solution was then concentrated. Triuration with acetone yielded 3.72 g (74.4% yield) of a nicely crystalline white solid. A second crop of 0.21 g of solid was obtained. The total yield was 78.5%; mp 98°-100° C.

NMR(d$_6$-DMSO): 9.35 (b, 1H), 4.86 (bs, 1H), 3.41 (d, J=20 Hz, 1H), 3.28 (d, J=20 Hz, 1H), 2.47-2.15 (m, 2H), 1.66 (dd, J=11 Hz, 2H), 1.20 (s, 3H)

MS: m/e 145 (18%); 127 (17%); 99 (44%); 82 (15%); 71 (19%); 58 (50%); 43 (100%).

IR: 1633 cm$^{-1}$ (C=O).

EXAMPLE 5

2-Chloro-5-methyl pyridine

To a suspension of 1.14 g (7.85 mmol) of 1,5-dihydroxy-5-methyl-2-piperidinone in 15 ml of methylene chloride was added dropwise 3.4 ml (47.1 mmol) of thionyl chloride. The reaction mixture was stirred at slightly above room temperature for 23 hours. The mixture was then basified carefully with saturated aqueous sodium bicarbonate and partitioned with methylene chloride. The organic solution was dried with Na$_2$SO$_4$ and concentrated to yield an orange-red liquid of about 87% purity by GC. The weight obtained was about 650 mg (65% yield). This material had a proton NMR spectrum and GC retention time identical to a known sample.

What is claimed is:

1. A method for the preparation of a 2-halo-5-methyl-pyridine of the following formula (I):

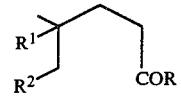

wherein X is a halogen atom, said method comprising the steps of:

(a) reacting a 4-methyl-4-pentene derivative of the following formula (II):

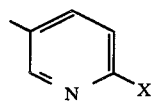

wherein R is a halo, aryloxy or alkoxy group with a halohydrination, haloalkanoyloxylation, halogenation or oxidation agent to produce a pentane derivative of the following formula (III):

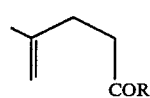

wherein $R^1$ and $R^2$ are (i) independently alkanoyloxy, hydroxy or halogen groups or (ii) are joined together to form a 3-membered heterocyclic ring;

(b) reacting the pentane derivative of formula (III) with an amine to produce a pyridone of the following formula (IV):

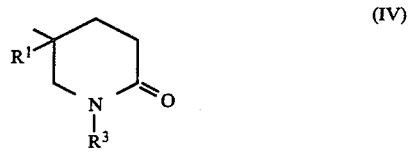

wherein $R^3$ is alkoxy, alkanoyloxy or hydroxy; and (c) reacting the pyridone of formula (IV) with a halogenation agent to produce the 2-halo-5-methylpyridine of formula (I).

2. The method of claim 1, wherein X is a chlorine or bromine atom.

3. The method of claim 2, wherein X is a chlorine atom.

4. The method of claim 1, wherein R is an alkoxy group of about 1 to 6 carbons.

5. The method of claim 1, wherein $R^1$ and $R^2$ are independently hydroxy, chlorine or bromine groups or are joined to form an oxirane ring.

6. The method of claim 5, wherein $R^1$ is hydroxy and $R^2$ is bromine; $R^1$ is hydroxy and $R^2$ is chlorine; $R^1$ and $R^2$ are both bromine; $R^1$ and $R^2$ are both chlorine; or $R^1$ and $R^2$ are joined to form an oxirane ring.

7. The method of claim 1, wherein $R^3$ is hydroxy.

8. The method of claim 1, wherein in step (b), said amine is methoxyamine hydroxylamine or a salt thereof.

9. The method of claim 1, wherein in step (c), said halogenation agent is selected from the group consisting of oxalyl chloride, thionyl bromide, thionyl chloride, phosgene or phosphorus oxychloride.

10. The method of claim 1, wherein in step (a), said halohydrination agent is selected from the group consisting of sodium hypohalite, N-bromosuccinimide, N-chlorosuccinimide, bromine, 1,3-dibromo-5,5-dimethylhydantoin, 1,3-dichloro-5,5-dimethylhydantoin, chloramine-T hydrate, N-bromoacetamide and N-chloroacetamide.

11. The method of claim 1, wherein in step (a), said haloalkanoyloxylation agent is a hypohalite of an aliphatic carboxylic acid of about 2-4 carbons.

12. The method of claim 11, wherein said haloalkanoyloxylation agent is acetyl hypobromite or propanoyl hypochlorite.

13. The method of claim 11, wherein said hypohalite of an aliphatic carboxylic acid is the reaction product of an aliphatic carboxylic acid of about 2 to 4 carbons or a salt thereof and a compound selected from the group consisting of sodium hypohalite, N-bromosuccinimide, N-chlorosuccinimide, bromine, 1,3-dibromo-5,5-dimethylhydantoin, 1,3-dichloro-5,5-dimethylhydantoin, chloramine-T hydrate, N-bromoacetamide and N-chloroacetamide.

14. The method of claim 13, wherein said hypohalite of an aliphatic carboxylic acid is the reaction product of chloramine-T hydrate with acetic acid or N-bromoacetamide with lithium acetate.

15. The method of claim 1, wherein in step (a), said halogenation agent is chlorine or bromine.

16. The method of claim 1, wherein in step (a), said oxidation agent is a peracid of the formula $R^4$—COOOH wherein $R^4$ is alkyl or an alkylhydroperoxide with a transition metal catalyst.

17. The method of claim 16, wherein said oxidation agent is selected from the group consisting of peracetic acid, peroxytrifluoroacetic acid, perbenzoic acid, monoperphthalic acid and meta-chloroperbenzoic acid.

18. The method of claim 16, wherein said oxidation agent is tert-butylhydroperoxide with vanadium or hydrogen peroxide with tungsten.

19. A method for the preparation of a 3-chloro-2-halo-5-methylpyridine of the following formula (V):

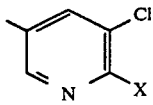

wherein X is a halogen atom, said method comprising the steps of:
(a) reacting a 4-methyl-4-pentene derivative of the following formula (II):

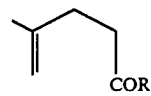

wherein R is a halo, aryloxy or alkoxy group, with chlorine to produce a pentane derivative of the following formula (VI):

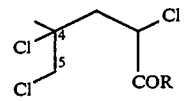

(b) reacting the pentane derivative of formula (VI) with an amine to produce a pyridone of the following formula (VII):

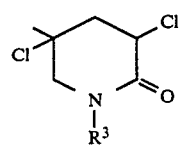

wherein $R^3$ is alkoxy, alkanoyloxy or hydroxy; and
(c) reacting the pyridone of formula (VII) with a halogenation agent to produce the 3-chloro-2-halo-5-methyl-pyridine of formula (V).

* * * * *